(12) United States Patent
Albrecht

(10) Patent No.: US 8,097,000 B2
(45) Date of Patent: Jan. 17, 2012

(54) HYBRID LAPAROSCOPIC-ENDOSCOPIC SURGICAL TECHNIQUE FOR DELIVERING END EFFECTORS THROUGH A NATURAL ORIFICE

(75) Inventor: Thomas E. Albrecht, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 899 days.

(21) Appl. No.: 12/113,735

(22) Filed: May 1, 2008

(65) Prior Publication Data

US 2009/0275797 A1     Nov. 5, 2009

(51) Int. Cl.
*A61F 11/00* (2006.01)
(52) U.S. Cl. .......................... 606/108; 606/151; 600/101
(58) Field of Classification Search .................. 606/108, 606/191, 139, 151, 232; 600/37, 101; 604/93.01, 604/104, 164.1, 175
See application file for complete search history.

(56) References Cited

U.S. PATENT DOCUMENTS

| 4,134,405 A * | 1/1979 | Smit ............................. 606/108 |
| 5,817,111 A * | 10/1998 | Riza ............................. 606/148 |
| 2007/0225728 A1* | 9/2007 | Stefanchik et al. ........... 606/108 |

* cited by examiner

*Primary Examiner* — Gary Jackson
*Assistant Examiner* — Katherine Dowe
(74) *Attorney, Agent, or Firm* — Welsh Flaxman & Gitler LLC

(57) ABSTRACT

A method for performing a hybrid laparoscopic-endoscopic procedure is achieved by inserting a medical instrument laparoscopically through an abdominal wall and into a gastric cavity, inserting an overtube and endoscope transorally into the gastric cavity to provide an access path to the gastric cavity, passing an end effector transorally to the surgical site translumenally within the endoscope, and attaching the end effector to a distal end of the medical instrument while the instrument is positioned within the gastric cavity.

16 Claims, 4 Drawing Sheets

HYBRID LAPAROSCOPIC-ENDOSCOPIC SURGICAL TECHNIQUE FOR DELIVERING END EFFECTORS THROUGH A NATURAL ORIFICE

BACKGROUND OF THE INVENTION

1. Field of the Invention

The present invention relates to surgical techniques and medical instruments therefore. More particularly, the present invention relates to a technique and associated medical instruments for performing hybrid laparoscopic-endoscopic surgical procedures in which end effectors are delivered through a natural orifice.

2. Description of the Related Art

Obesity is a medical condition affecting more than 30% of the population in the United States. Obesity affects an individual's personal quality of life and contributes significantly to morbidity and mortality. Obese patients, i.e., individuals having a body mass index ("BMI") greater than 30, often have a high risk of associated health problems (e.g., diabetes, hypertension and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients. Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

It is known to create gastric cavity wall plications through endoscopic only procedures. However, operating solely within the interior of the gastric cavity limits the plication depth that can be achieved without cutting. Furthermore, access and visibility within the gastric and peritoneal cavities is limited in a purely endoscopic procedure as the extent of the reduction increases.

As discussed above, a number of different types of surgical procedures may be performed within a gastric cavity. These procedures can include treatments for GERD, as well as gastric volume reductions for the treatment of morbid obesity. During these surgical procedures, one or more incisions are typically made through the abdominal wall to reach the gastric cavity. These incisions must be made large enough to accommodate surgical tools. Even in a laparoscopic procedure, the incisions must be made large enough to accommodate not only the device shaft, but also a variety of distal end effectors, such as staplers, suturing devices, and the like. These end effectors usually require a larger diameter than the mechanics within the device shaft and require the use of a larger trocar. Patient discomfort, recovery time and infection risk increase with the increasing size of an incision site. Accordingly, it is desirable to provide a technique for performing gastric cavity surgery through a minimally-sized incision.

With the foregoing in mind, it is desirable to provide surgical weight loss procedures (and associated medical instruments) that are inexpensive, with few potential complications, and that provide patients with a weight loss benefit while buying time for the lifestyle changes necessary to maintain the weight loss. Further, it is desirable that the procedures be minimally invasive to the patient, allowing for a quick recovery and less scarring. The present invention provides such a procedure and associated medical instruments.

SUMMARY OF THE INVENTION

It is, therefore, an object of the present invention to provide a method for performing a hybrid laparoscopic-endoscopic procedure. The method is achieved by inserting a medical instrument laparoscopically through an abdominal wall and into a gastric cavity, inserting an overtube and endoscope transorally into the gastric cavity to provide an access path to the gastric cavity, passing an end effector transorally to the surgical site translumenally within the endoscope, and attaching the end effector to a distal end of the medical instrument while the instrument is positioned within the gastric cavity.

It is also an object of the present invention to provide a method wherein the step of inserting includes inserting the medical instrument through an abdominal wall and gastric wall such that only a portion of the medical instrument protrudes into a gastric cavity.

It is another object of the present invention to provide a method wherein the step of inserting includes passing a trocar to the gastric cavity for facilitating the passage of the medical instrument to the gastric cavity.

It is a further object of the present invention to provide a method wherein the step of passing an end effector includes securing the end effector to a distal end of a grasper and guiding the end effector to a desired location within the gastric cavity.

It is another object of the present invention to provide a method wherein the medical instrument includes a shaft having an inner cylinder and an outer cylinder, the inner cylinder and outer cylinder being concentric, and a rod extends axially through the center of the inner and outer cylinders, a locking element is secured to a distal end of the inner cylinder.

It is a further object of the present invention to provide a method wherein the end effector includes a housing extending proximally from an operative element of the end effector, the housing includes a lateral slot shaped and dimensioned for engaging the locking element on the inner cylinder of the shaft of the medical instrument.

It is also an object of the present invention to provide a method wherein a notch is located within the operative element of the end effector, the notch engages a driving mechanism on a distal end of the rod when the medical instrument is connected to the end effector.

It is another object of the present invention to provide a method wherein the step of inserting includes passing a trocar to the abdominal cavity for facilitating the passage of the medical instrument to the abdominal cavity.

It is a further object of the present invention to provide a method wherein the step of passing an end effector includes securing the end effector to a distal end of a grasper and guiding the end effector to a desired location within an abdmoninal cavity.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 5, a hybrid endoscopic/laparoscopic surgical technique is disclosed. As used throughout the present specification the term endoscopic is used to refer to surgical procedures in which body access is achieved via a natural orifice (for example, transorally) and the term laparoscopic is used to refer to surgical procedures in which body access is achieved via a surgically created opening (for example, through the use of a trocar). The present procedure allows for the utilization of a conventional large diameter laparoscopic medical instrument without the need for the creation of large incisions and the use of large trocars otherwise required for the passage of the large diameter end effectors into the gastric cavity. Although the present procedure is described herein for use in performing gastric procedures, those skilled in the art will appreciate the underlying concepts of the present invention may be applied in conjunction with other procedures without departing from the spirit of the present invention.

Figure 1:
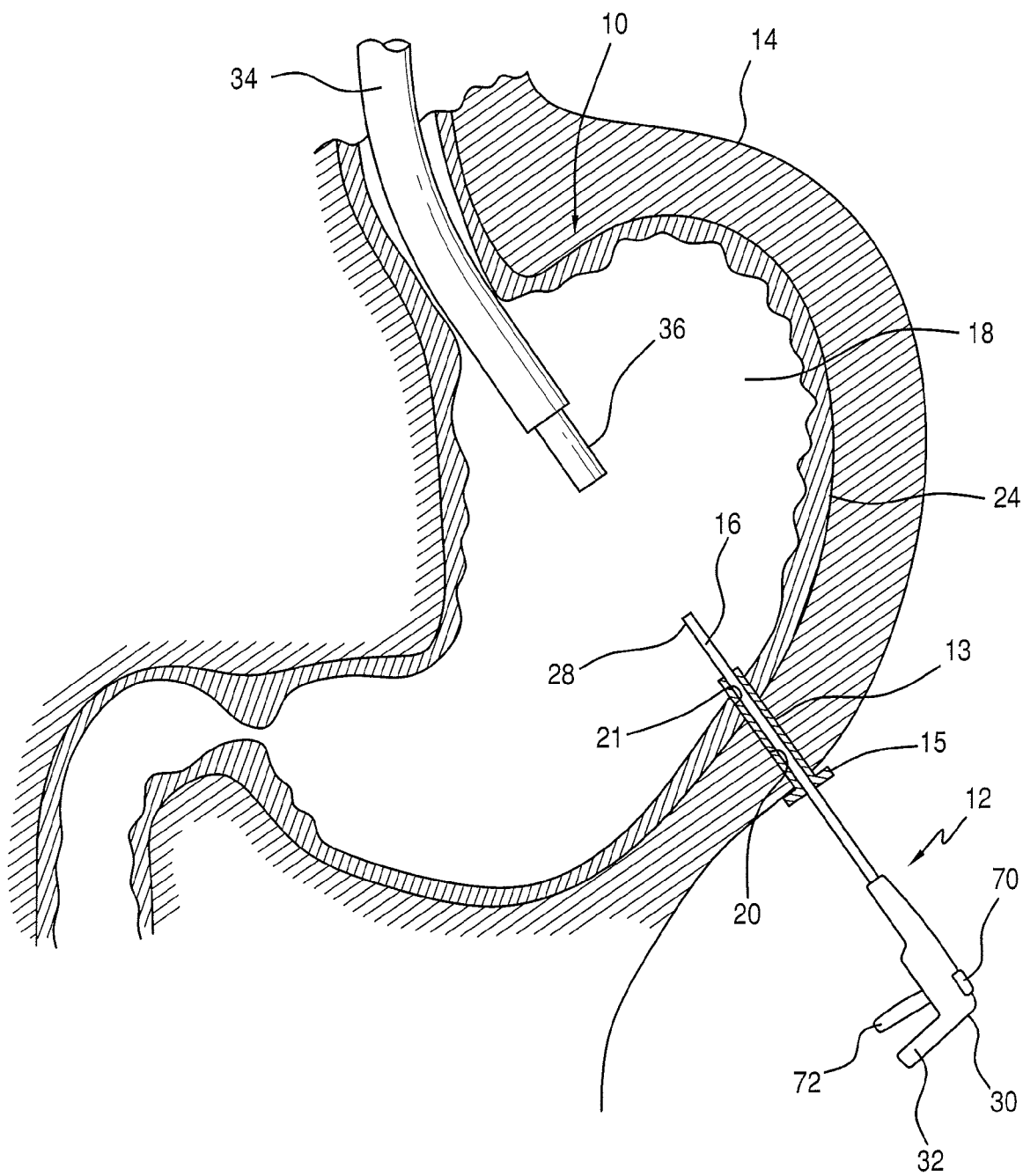
FIG. 1 is a schematic view of a gastric cavity prepared for a laparoscopic-endoscopic procedure.

FIG. 1 is a schematic view of a gastric cavity 10 at the initiation of a laparoscopic/endoscopic hybrid procedure in accordance with a preferred embodiment of the present invention. As shown in FIG. 1, a medical instrument 12 is inserted through an abdominal wall 14 and gastric wall 24 such that the shaft 16 of the medical instrument 12 protrudes into a gastric cavity 18. Incision 20 having a length just slightly longer than the diameter of the trocar 15 is made through the abdominal wall. The trocar 15 is then inserted through incision 20 until it reaches the gastric wall 24. Thereafter, a second incision 21 is made in the gastric wall 24 to accommodate the lumen 13 of the trocar 15. Passage of the shaft 16 of the medical instrument 12 into the gastric cavity 18 is facilitated by first passing a trocar 15 through the incisions 20, 21. The trocar 15 is sized to accommodate the shaft 16 of the medical instrument 12 therethrough, and is first passed through the incisions 20, 21 to stabilize the opening. The medical instrument 12 may then be passed through the trocar 15 with the distal end 28 of the medical instrument 12 within the gastric cavity 18 with the proximal end 30 of the medical instrument 12 external of the patient for manipulation by a medical practitioner. A handle 32 is located at the proximal end 30 of the medical instrument 12 to control the operation of the medical instrument 12.

In accordance with a preferred embodiment of the present procedure, an overtube 34 and endoscope 36 are inserted transorally into the gastric cavity 18 to provide a secondary access path to the gastric cavity 18. With the medical instrument 12 and the overtube 34 positioned within the gastric cavity 18, an end effector 38 is passed to the surgical site translumenally within the endoscope 36, as shown in F*igure* 2. In accordance with a preferred embodiment, the end effector 38 is secured to the distal end 40 of a grasper 42 which is then used to guide the end effector 38 to a desired location within the gastric cavity 18. The endoscope 36 is inserted through a natural orifice, more specifically the mouth, rather than an incision, and is, therefore, better suited to pass the larger diameter end effector 38 of the medical instrument 12 into the gastric cavity 18. The end effector 38 is passed translumenally through the overtube 34 using a grasper 42 as shown, or any other type of device capable of holding the end effectors stable during passage.

Figure 3:
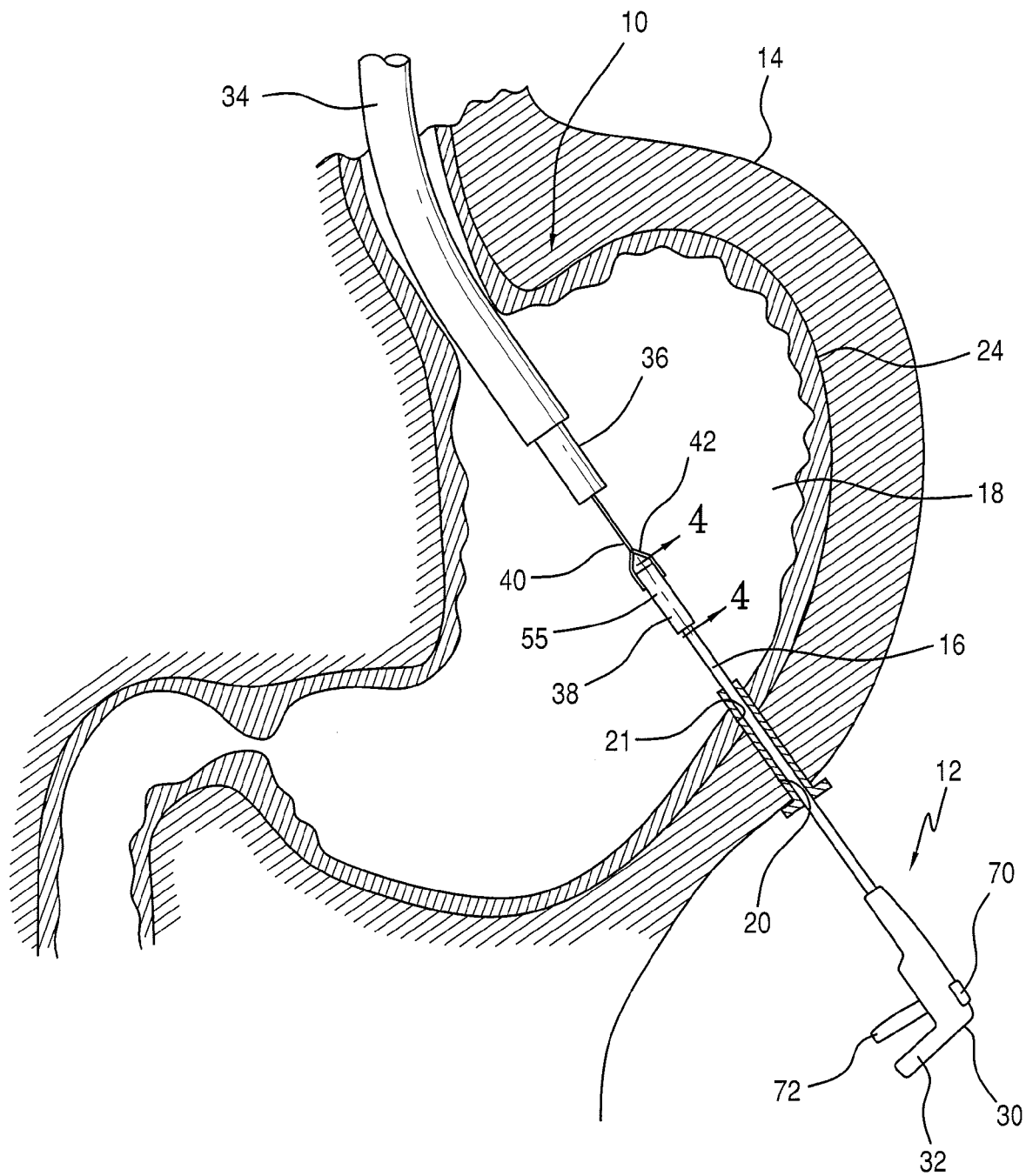
FIG. 3 is a schematic view of an end effector being connected to a device shaft.
Figure 4:
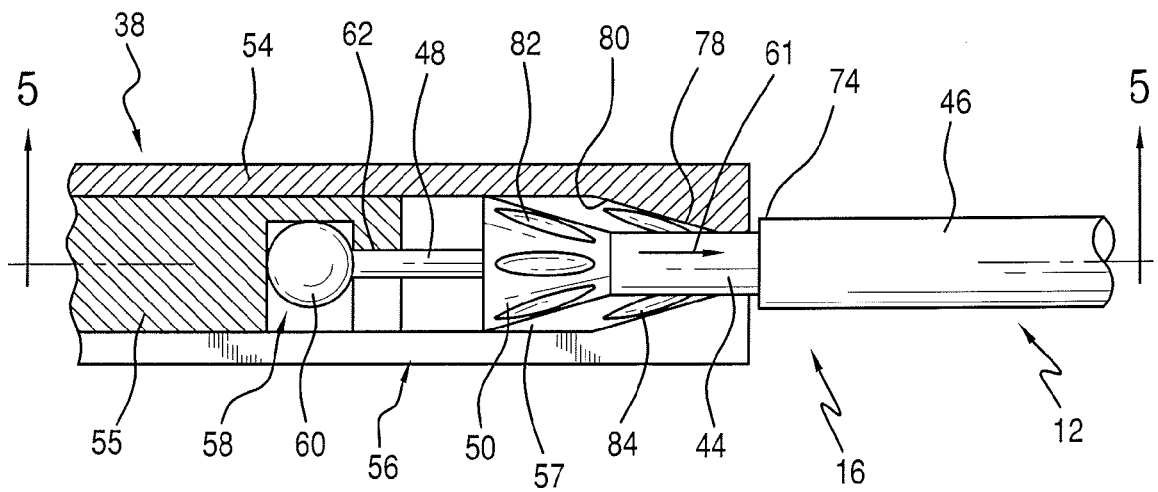
FIG. 4 is a cross-sectional view taken along line 4-4 of FIG. 3, showing an exemplary attachment mechanism between a device and an end effector.
Figure 5:
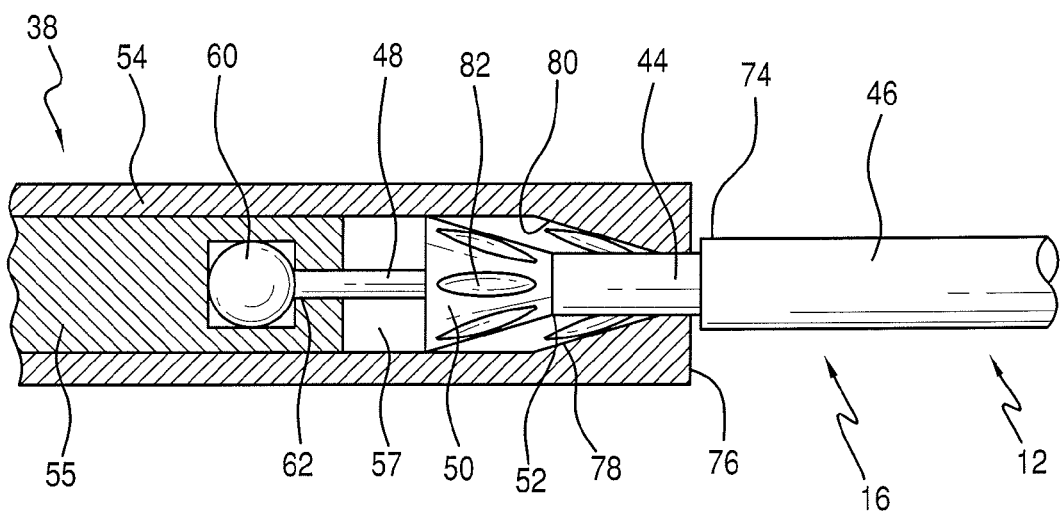
FIG. 5 is a cross-sectional view taken along line 5-5 of FIG. 4, showing an exemplary attachment mechanism between a device and an end effector.

Once inside the gastric cavity 18, the end effector 38 is attached to the distal end 28 of the shaft 16 of the medical instrument 12, as shown in FIG. 3. The end effector 38 and the medical instrument 12 may be attached by a variety of different types of fastening mechanisms. FIGS. 4 and 5 show an example of a mechanism for connecting an end effector 38 to the medical instrument 12 in accordance with a preferred embodiment of the present invention.

As shown in FIGS. 4 and 5, the shaft 16 of the medical instrument 12 comprises a pair of concentric cylinders 44, 46 and a rod 48 extending axially through the center of the cylinders 44, 46. A locking element 50 is retained on the distal end 52 of the inner cylinder 44. The locking element 50 is shaped and dimensioned for engaging the end effector 38 in a manner securely coupling the shaft 16 of the medical instrument 12 to the end effector as is discussed below in greater detail. The locking element 50 is longitudinally moveable relative to the cylinder 46. The relative positioning of the locking element 50 is controlled by a locking toggle 70 actuated at the handle 32 of the medical instrument 12 for selectively controlling when the locking element 50 is permitted to move relative to the cylinder 46 and when it is selectively locked in position.

The medical instrument also includes a driving mechanism 60 secured to the distal end 62 of the rod 48. The driving mechanism 60 is shaped and dimensioned for engagement with the operative element 55 (for example, the stapling mechanism of a surgical stapler end effector or the pivoting arms of a grasper end effector) and the rod 48 to which the driving mechanism is secured is moved linearly under the control of the trigger 72 of the handle 32 for actuation of the operative element 55 of the end effector 38 as the driving element is moved forward and backward to transfer motion to the operative element 55 of the end effector 38.

The end effector 38 includes a housing 54 extending proximally from the operative element 55 of the end effector 38. The housing 54 includes a lateral slot 56 shaped and dimensioned for receiving the locking element 50 and driving mechanism 60 respectively secured to the distal ends 52, 62 of the cylinder 44 and rod 48 for ultimate attachment of the end effector 38 to the shaft 16 of the medical instrument 12. The slot 56 provides access to a recess 57 formed in the housing 54 of the end effector 38, and into which the locking element 50 and driving mechanism 60 are positioned for coupling of the shaft 16 of medical instrument 12 with the end effector 38.

The operative element 55 of the end effector 38 includes a notch 58 which is accessible through the lateral slot 56. The notch 58 is shaped and dimensioned for receiving and coupling to the driving mechanism 60 on the distal end 62 of the rod 48 when the medical instrument 12 is connected to the end effector 38. In this way movement of the driving mechanism 60 is transferred to the operative element 55 of the end effector 38 for facilitating movement thereof in accordance with the intended functionality of the end effector 38.

After the end effector 38 is passed into the gastric cavity 10, the locking element 50 is inserted through the slot 56 and into the recess 57 as the driving mechanism 60 is positioned and securely seated within the notch 58. With the distal end 28 of the medical instrument 12 inserted into the end effector housing 54 and the distal end 74 of the cylinder 46 abutting the proximal end 76 of the housing 54, the locking element 50 is pulled proximally by the inner cylinder 44, as indicated by the arrow 61. As the locking element 50 is pulled proximal it seats within the proximal end 78 of the recess 57. More particularly, the locking element 50 is preferably frustoconically shaped and the inner proximal surface 80 of the recess 57 is similarly frustoconically shaped to receive the locking element 50 in a manner locking the medical instrument 12 to the end effector 38 via the interaction of the distal end 74 of the cylinder 46 abutting the proximal end 76 of the housing 54 with distal force and the locking element 50 seating within the inner proximal surface 80 of the recess 57 with proximal force. Alignment and secure coupling of the locking element 50 within the inner proximal surface 80 is achieved by providing the locking element 50 and the inner proximal surface 80 with respective recesses 82 and protrusions 84 shaped and dimensioned to mate as the locking element 50 is pulled into the inner proximal surface 80. The proximal end 76 of the recess 57 is of reduced diameter to restrain the locking element 50 when the locking element 50 is shifted proximally against the inner proximal surface 80 of the recess 57. With the locking element 50 restrained within the housing 54, the medical instrument 12 is connected to the end effector 38. Accordingly, backward and forward movement of the rod 48 by the trigger 70 of the handle 32 will produce a corresponding movement in the end effector 38 operative element, thereby driving the instrument.

A number of different types of end effectors, such as, for example, linear or circular staplers, cutters, graspers, suturing devices, or other surgical instruments may be connected to the distal end of the medical instrument to perform a procedure. When a surgeon is finished with the end effector 38, the grasper 42 is used to hold the end effector 38 while the inner cylinder 44 is pushed distally by the handle 32 to release the end effector 38 from the shaft 16. The released end effector 38 is drawn back through the overtube 34 by the grasper 42 and pulled outside of the body. If necessary, a second end effector may be attached to the grasper and passed through the overtube into the gastric cavity. Inside the gastric cavity, the second end effector is then attached to the medical instrument in the same manner as the first end effector. After attachment, the second end effector is driven by the handle to continue the surgical procedure.

In a laparoscopic-endoscopic hybrid procedure in accordance with the concepts underlying the present invention, only the shaft 16 of a medical instrument 12 is passed through the incision opening 20, 21. The end effectors 38 that are used to engage the gastric tissue are introduced to the surgical site transorally. Passing the larger sized surgical tools transorally enables a smaller diameter trocar to be used in the laparoscopic passage of the medical instrument 12 through the incision. By reducing the size of the incision, scarring and the risk of infection are reduced.

Figure 2:
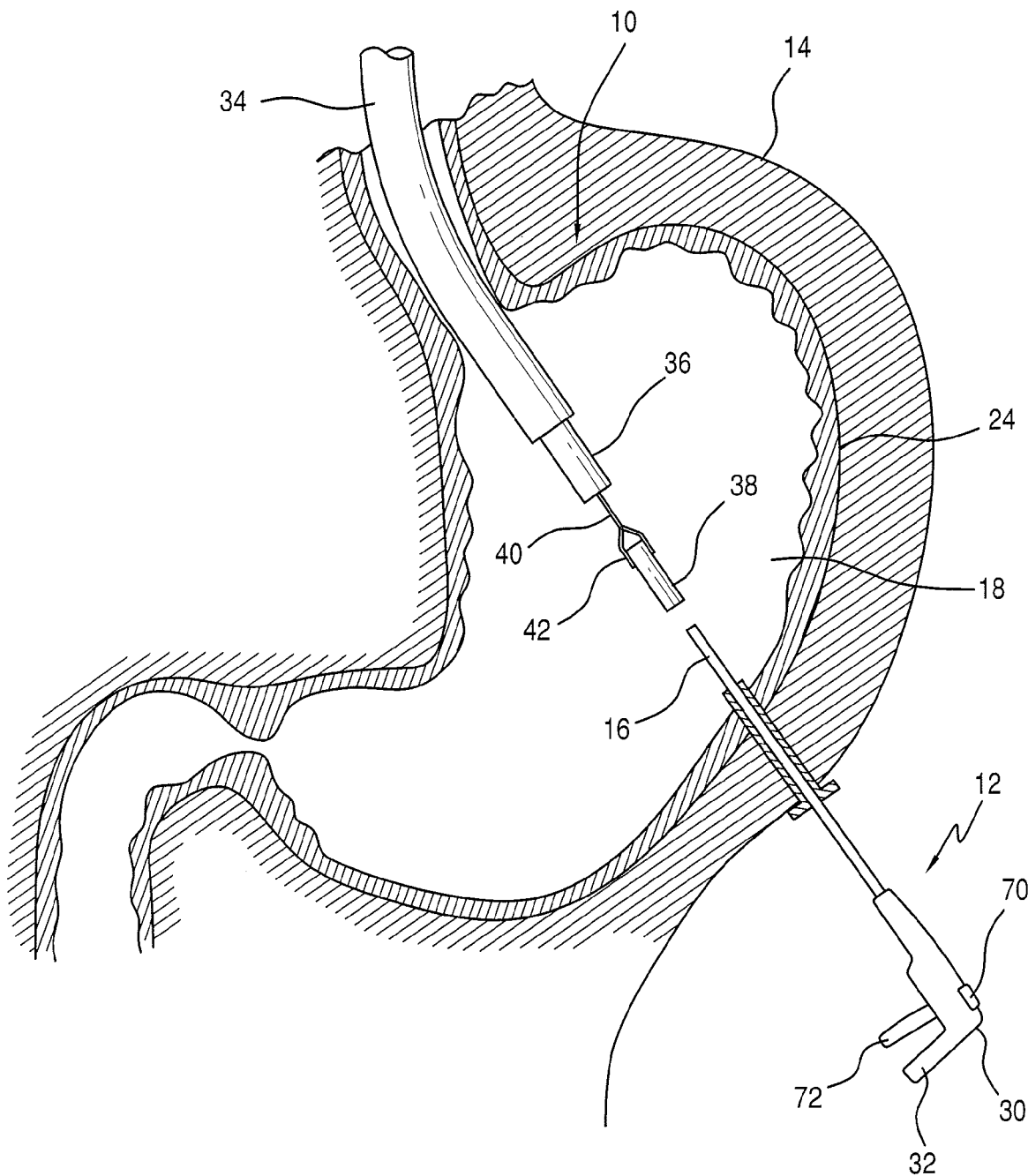
FIG. 2 is a schematic view similar to FIG. 1, showing an end effector being passed through an overtube into a gastric cavity.

FIGS. 1 to 3 depict a single incision and shaft 16 of the medical instrument 12 for performing the surgical procedure. In this embodiment, the endoscope 36 is used to visualize the procedure. In an alternative embodiment, however, a second laparoscopic opening may be made into the gastric cavity to allow a second device or laparoscope to be introduced into the cavity to aid in the procedure.

Alternatively, this technique can be used for performing procedures in the peritoneal cavity by passing the device end effectors translumenally and attaching to device shafts placed into the site through small abdominal incisions.

The concepts underlying the present invention, that is, a reverse transgastric approach to hybrid laparoscopic/endoscopic procedures allows end effectors to be delivered transorally with subsequent attachment to a medical instrument accessed laparoscopically through, for example, the gastric wall, to reduce the size of the incision necessary for the procedure which results in a reduction in the trauma to the body, for example, the abdomen.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, and/or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for performing a hybrid laparoscopic-endoscopic procedure, comprising:
    inserting a medical instrument laparoscopically through an abdominal wall and into a gastric cavity, the medical instrument including a distal end within the gastric cavity and a proximal end external of the gastric cavity, the proximal end including a handle for controlling operation of a driving mechanism of the medical instrument;
    inserting an overtube transorally into the gastric cavity to provide an access path to the gastric cavity;
    passing an end effector transorally to a surgical site through the overtube, the end effector including an operative element;
    attaching the end effector to the distal end of the medical instrument while the medical instrument is positioned within the gastric cavity, wherein the step of attaching includes securing the driving mechanism to the operative element of the end effector permitting the transfer of motion to the operative element based upon actuation of the handle; and
    using the operative element of the end effector to perform a procedure within the gastric cavity while the end effector is attached to the medical instrument, wherein actuation of the operative element is controlled by actuation of the handle.

2. The method according to claim 1, wherein the step of inserting includes inserting the medical instrument through the abdominal wall and gastric wall such that only the distal end of the medical instrument protrudes into the gastric cavity.

3. The method according to claim 2, wherein the step of inserting includes passing a trocar to the gastric cavity for facilitating the passage of the medical instrument to the gastric cavity.

4. The method according to claim 2, wherein the step of passing the end effector includes securing the end effector to a distal end of a grasper and guiding the end effector to a desired location within the gastric cavity.

5. The method according to claim 1, wherein the medical instrument includes a shaft composed of an inner cylinder and an outer cylinder, the inner cylinder and the outer cylinder being concentric, and a rod extends axially through a center of the inner and outer cylinders and the driving mechanism is secured to a distal end of the rod, a locking element is secured on a distal end of the inner cylinder.

6. The method according to claim 5, wherein the end effector includes a housing extending proximally from the operative element of the end effector, the housing includes a lateral slot shaped and dimensioned for engaging the locking element on the inner cylinder of the shaft of the medical instrument.

7. The method according to claim 6, wherein a notch is located within the operative element of the end effector, the notch engages the driving mechanism on the distal end of the rod when the medical instrument is connected to the end effector.

8. The method according to claim 7, wherein the handle includes a trigger secured to the rod for actuation of the driving mechanism causing transfer of motion to the operative element of the end effector.

9. The method according to claim 8, wherein the rod is moved linearly upon actuation of the handle.

10. The method according to claim 7, wherein the rod is moved linearly upon actuation of the handle.

11. The method according to claim 1, wherein the step of inserting includes passing a trocar to an abdominal cavity for facilitating the passage of the medical instrument to the abdominal cavity.

12. The method according to claim 1, wherein the step of passing an end effector includes securing the end effector to a distal end of a grasper and guiding the end effector to a desired location within an abdominal cavity.

13. The method according to claim 1, wherein the handle includes a trigger for actuation of the driving mechanism causing transfer of motion to the operative element of the end effector.

14. The method according to claim 1, wherein the medical instrument includes a rod extending between the handle and the driving mechanism for moving the operative element.

15. The method according to claim 14, wherein the rod is moved linearly upon actuation of the handle.

16. The method according to claim 15, wherein the handle includes a trigger for actuation of the rod in a linear direction.

* * * * *